United States Patent
Kim et al.

(10) Patent No.: US 10,464,866 B2
(45) Date of Patent: Nov. 5, 2019

(54) APPARATUS AND METHOD FOR PURIFYING CUMENE

(71) Applicant: LG CHEM, LTD., Seoul (KR)

(72) Inventors: Sung Kyun Kim, Daejeon (KR); Sung Kyu Lee, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 378 days.

(21) Appl. No.: 15/304,017

(22) PCT Filed: May 22, 2015

(86) PCT No.: PCT/KR2015/005146
§ 371 (c)(1),
(2) Date: Oct. 13, 2016

(87) PCT Pub. No.: WO2015/178718
PCT Pub. Date: Nov. 26, 2015

(65) Prior Publication Data
US 2017/0044081 A1    Feb. 16, 2017

(30) Foreign Application Priority Data

May 22, 2014  (KR) .................. 10-2014-0061553

(51) Int. Cl.
 *C07C 7/04*  (2006.01)
 *B01D 3/14*  (2006.01)

(52) U.S. Cl.
 CPC ............... *C07C 7/04* (2013.01); *B01D 3/141* (2013.01); *B01D 3/143* (2013.01)

(58) Field of Classification Search
 CPC ......... C07C 7/04; C07C 15/085; B01D 3/141; B01D 3/143; C07B 63/00
 See application file for complete search history.

(56) References Cited

U.S. PATENT DOCUMENTS 5,600,049 A    2/1997 Sy
8,242,320 B2   8/2012 Schmidt
(Continued)

FOREIGN PATENT DOCUMENTS

CN    101679149 A    3/2010
EP      2520560 B1    6/2017
(Continued)

OTHER PUBLICATIONS

Alexandre C. Dimian et al., "Alkylation of Benzene by Propylene to Cumene", Chemical Process Design: Computer-Aided Case Studies, Mar. 3, 2008, pp. 173-200.

*Primary Examiner* — Renee Robinson
*Assistant Examiner* — Derek N Mueller
(74) *Attorney, Agent, or Firm* — Dentons US LLP

(57) ABSTRACT

The present application relates to an apparatus for purifying cumene comprising: a first dividing wall type distillation column which takes in a stream from an alkylation reactor and comprises a first benzene output line and a benzene/cumene/polyisopropylbenzene stream output line; a second dividing wall type distillation column which takes in a stream from a transalkylation reactor and a benzene/cumene/polyisopropylbenzene stream, includes a transalkylation reactor stream input line, a benzene/cumene/polyisopropylbenzene stream input line, a second benzene output line, and a first polyisopropylbenzene stream output line; and a third distillation column which takes in a polyisopropylbenzene stream, includes a second polyisopropylbenzene output line, and a heavies output line.

11 Claims, 2 Drawing Sheets

(56) References Cited

U.S. PATENT DOCUMENTS 8,445,738 B2 5/2013 Hwang et al.
2008/0289946 A1* 11/2008 Schultz .................... B01D 3/14
  202/153

FOREIGN PATENT DOCUMENTS

| JP | 2007-514786 A | 6/2007 |
|---|---|---|
| KR | 1020110082160 A | 7/2011 |
| KR | 1020120102912 A | 9/2012 |
| KR | 1020130008595 A | 1/2013 |
| KR | 1020130120200 A | 11/2013 |
| WO | 2014003732 A1 | 1/2014 |

* cited by examiner

[Fig. 1]
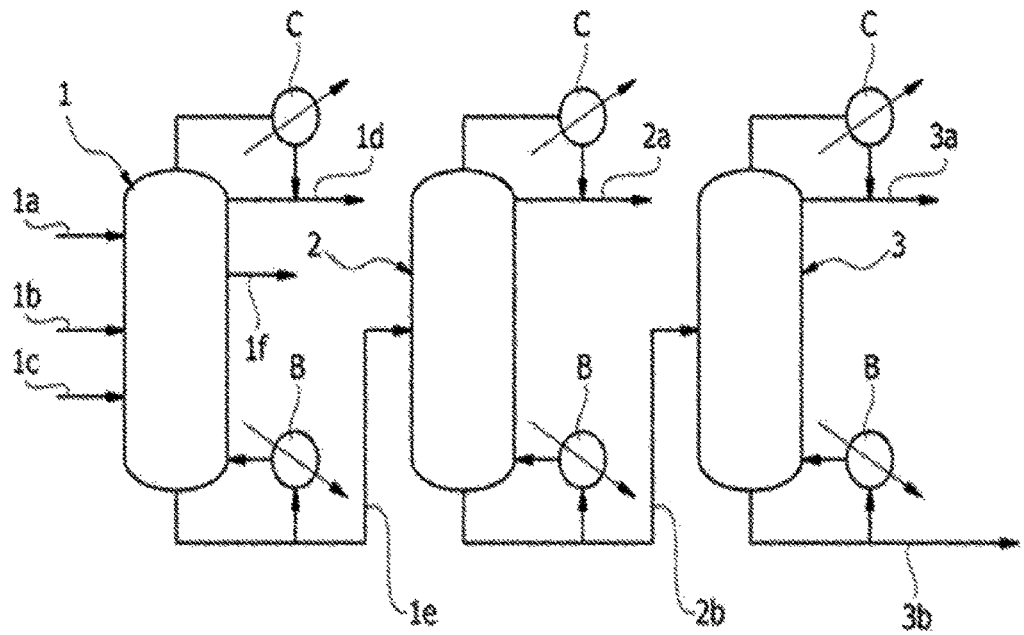
[Fig. 2]
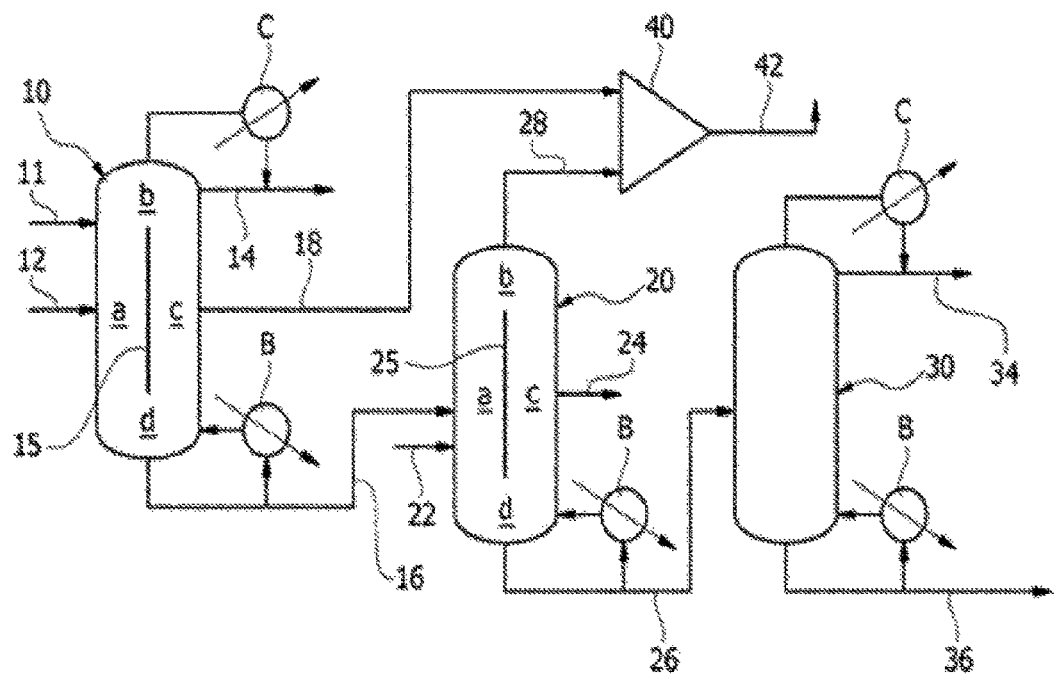

[FIG. 3] - RELATED ART
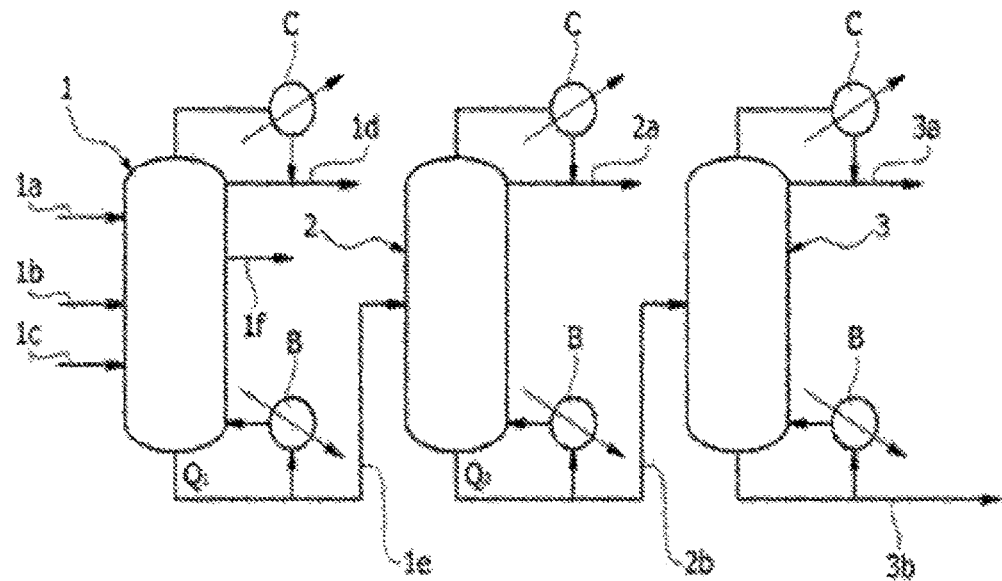
[FIG. 4]
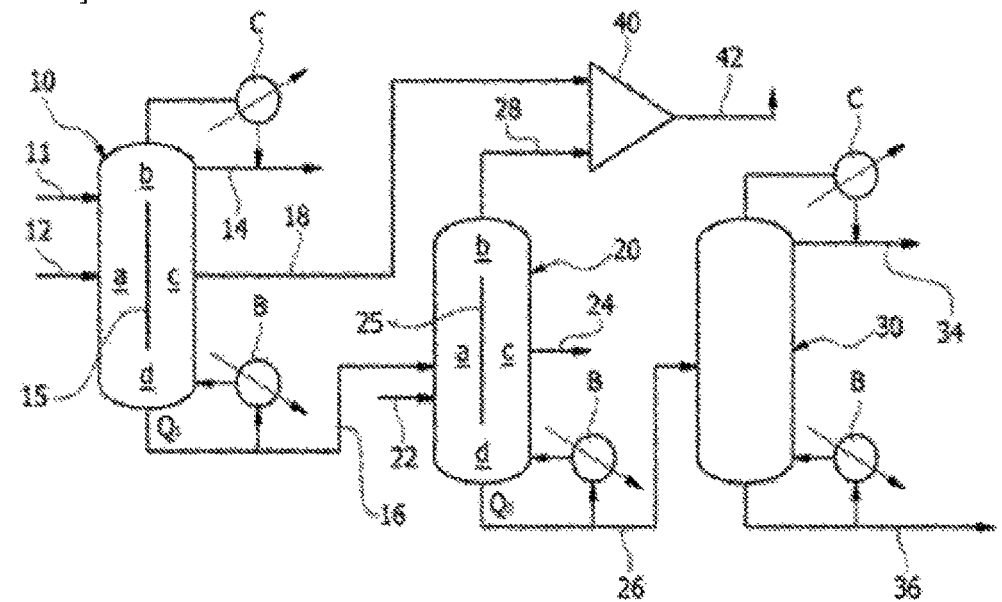

APPARATUS AND METHOD FOR PURIFYING CUMENE

This application is a National Stage Application of International Application No. PCT/KR2015/005146, filed on May 22, 2015, and claims the benefit of Korean Patent Application No. 10-2014-0061553, filed on May 22, 2014, the contents of which are incorporated herein by reference in their entirety for all purposes as if fully set forth below.

TECHNICAL FIELD

The present application relates to an apparatus and method for purifying cumene.

Specifically, the present application relates to an apparatus and method for purifying cumene to increase the energy efficiency in the purification process.

BACKGROUND ART

Cumene is isopropylbenzene ($C_6H_5CH(CH_3)_2$), and it is used as an important intermediate material in a variety of chemical industries, polymer industries, etc. At present, most of the cumene (isopropylbenzene) being produced is used for the preparation of phenol, acetone, etc.

Cumene is generally produced by reacting benzene and propylene under liquid or gas phase conditions in the presence of a catalyst. Technologies related to the preparation of cumene are proposed in Korean Unexamined Patent Application Publication No. 10-2011-0082160 and Korean Unexamined Patent Application Publication No. 10-2013-0008595, etc.

Cumene is mostly commercially prepared through an alkylation reaction and a trans alkylation reaction. Accordingly, an apparatus for preparing cumene includes an alkylation reaction unit and a trans alkylation reaction unit.

In the alkylation reaction unit, benzene and propylene react to produce cumene (isopropylbenzene) and, as a by-product, polyisopropylbenzenes (PIPB) such as diisopropylbenzene (DIPB), triisopropylbenzene (TIPB), etc. are produced through a reaction between cumene and propylene. The competitive reaction in the preparation of cumene is a polyalkylation reaction. In other words, it is a side reaction which produces the above-described PIPB s such as DIPB, TIPB, etc.

The trans alkylation reaction unit is used to react polyalkylated benzene, which is the PIPB, etc. produced through the above-described side reaction, with benzene to produce additional cumene.

Also, in addition to the substances described above, light materials (lights) such as C3 (propylene, propane, etc.), etc. and heavy materials (heavies), which are heavier than PIPB, are produced as additional products during the preparation of cumene, and along with these materials, unconsumed benzene, water, etc. are present. Therefore, in the alkylation reaction unit and trans alkylation reaction unit, lights such as C3 (propylene, propane, etc.), etc., PIPB, unconsumed benzene, water and other heavies, etc. are discharged in addition to the cumene (isopropylbenzene) of interest; these materials are either removed or recycled through a purification process in pursuit of high purity cumene.

In general, three distillation columns are used in the purification process of cumene. FIG. 1 is a diagram illustrating the configuration of an apparatus for purifying cumene according to the prior art. Referring to FIG. 1, the purification process for cumene according to the prior art can be schematically illustrated as follows.

The apparatus for purifying cumene is generally installed in connection with the above-described alkylation reaction unit and trans alkylation reaction unit, and includes 3 distillation columns such as a first distillation column, a second distillation column and a third distillation column.

The first distillation column is a benzene column 1 which recovers benzene from streams from the alkylation reaction unit and trans alkylation reaction unit.

In this case, an in-put line 1b which takes in a stream discharged from the alkylation reaction unit and an in-put line 1c which takes in a stream discharged from the trans alkylation reaction unit are connected to the front end portion of the benzene column 1. Also, an in-put line 1a through which fresh benzene flows in is connected to the front end portion of the benzene column 1. In addition, lights such as C3, etc. and water are discharged from the upper portion of the benzene column 1 through a lights out-put line 1d, whereas a cumene stream is discharged from the lower portion through a cumene stream out-put line 1e. Further, benzene is discharged from substantially the center of the benzene column 1 through a benzene recycle line 1f, and the discharged benzene is recycled.

The second distillation column is a cumene column 2 which recovers cumene from the cumene stream discharged from the lower portion of the benzene column 1.

In this case, cumene is discharged from the upper portion of the cumene column 2 through a cumene out-put line 2a and recovered. Also, from the lower portion of the cumene column 2, a PIPB stream is discharged through a PIPB out-put line 2b.

The third distillation column is a PIPB column 3 which takes in and recycles the PIPB stream discharged from the lower portion of the cumene column 2.

In this case, PIPBs such as DIPB, etc. are discharged from the upper portion of the PIPB column 3 through a PIPB out-put line 3a and recycled. Also, from the lower portion of the PIPB column 3, heavies are discharged through a heavies out-put line 3b.

Cumene (isopropylbenzene) of interest can be purified to a high purity and recovered through a purification process such as the above. In addition, energy is consumed in the above-described purification process. To each of the columns 1, 2 and 3, a heat source is provided for the separation of substances by the differences in boiling points, and most of the energy is consumed in such a separation process. In FIG. 1, reference numeral C represents a condenser, and reference numeral B represents a heat exchanger (or reboiler) for supplying heat.

However, the cumene purification process according to the prior art requires a large consumption of energy. As described above, each of the columns 1, 2 and 3 is provided with a heat source for the separation of substances, and there is a problem in that the amount of energy consumed is large especially in such a separation process.

DISCLOSURE

Technical Problem

The present application provides an improved apparatus and method for purifying cumene.

With the apparatus and method for purifying cumene according to the present application, the energy consumed by supplementary devices such as a condenser, a heat exchanger, etc. can be saved.

Technical Solution

The present application is devised to solve the aforementioned problems, and relates to an apparatus for purifying cumene including:

a first dividing wall type distillation column which takes in a stream from an alkylation reaction unit, and includes a first benzene out-put line through which benzene is discharged and a lower out-put line through which a benzene/cumene/polyisopropylbenzene (PIPB) stream is discharged;

a second dividing wall type distillation column which takes in a stream from a trans alkylation reaction unit and the benzene/cumene/PIPB stream discharged through the lower out-put line of the first dividing wall type distillation column, and includes a second benzene out-put line through which benzene is discharged from the upper portion, and a PIPB stream out-put line through which a PIPB stream is discharged from the lower portion; and a third distillation column which takes in the PIPB stream discharged through the PIPB stream out-put line of the second dividing wall type distillation column, and includes a PIPB out-put line through which PIPB s are discharged from the upper portion, and a heavies out-put line through which heavies are discharged from the lower portion.

In addition, the apparatus for purifying cumene according to the present application may further include a combining unit through which the first benzene out-put line and second benzene out-put line are combined; and a benzene recycle line through which the benzene which is combined in the above-described combining unit is supplied to any one or more reaction units selected among the alkylation reaction unit and trans alkylation reaction unit.

In one example, the first benzene out-put line and second benzene out-put line may be operated in a way so as to satisfy Mathematical Formula 1 below.

$$BZ_1/BZ_2 = 1.0 \text{ to } 3.0 \qquad \text{[Mathematical Formula 1]}$$

(In the Mathematical Formula 1 above, $BZ_1$ represents the flow amount of benzene discharged through the first benzene line, whereas $BZ_2$ represents the flow amount of benzene discharged through the second benzene out-put line).

In addition, the present application relates to a method for purifying cumene, where the method includes:

a first separation process in which the stream from the alkylation reaction unit is introduced into the first dividing wall type distillation column, benzene is discharged through the first benzene out-put line, and the benzene/cumene/PIPB stream is discharged through the lower out-put line;

a second separation process in which the stream from the trans alkylation reaction unit and benzene/cumene/PIPB stream separated during the first separation process are introduced into the second dividing wall type distillation column, benzene is discharged through the second benzene out-put line, and the PIPB stream is discharged through the PIPB stream out-put line; and a third separation process in which the PIPB stream separated during the second separation process is introduced into the third distillation column, and PIPB s and heavies are separated.

In one example, the method for purifying cumene according to the present application may further include a step of combining the benzene discharged from the first benzene out-put line and second benzene out-put line, and supplying the combined benzene to any one or more reaction units selected among the alkylation reaction unit and trans alkylation reaction unit.

In one example, the first separation process and second separation process in the method for purifying cumene according to the present application may satisfy Mathematical Formula 1 below.

$$BZ_1/BZ_2 = 1.0 \text{ to } 3.0 \qquad \text{[Mathematical Formula 1]}$$

(In the Mathematical Formula 1 above, $BZ_1$ represents the flow amount of benzene discharged through the first benzene line, whereas $BZ_2$ represents the flow amount of benzene discharged through the second benzene out-put line).

Advantageous Effects

With the apparatus and method for purifying cumene according to the present application, the energy consumed by supplementary devices such as a condenser, a heat exchanger, etc. can be saved.

DESCRIPTION OF DRAWINGS

FIG. 1 is a diagram illustrating the configuration of an apparatus for purifying cumene according to the prior art.

FIG. 2 is a diagram illustrating the configuration of an apparatus for purifying cumene according to an embodiment of the present application.

FIG. 3 is a diagram illustrating the configuration of an apparatus for purifying cumene applied in a comparative example.

FIG. 4 is a diagram illustrating the configuration of an apparatus for purifying cumene applied in examples.

DESCRIPTION OF REFERENCE NUMERALS

10: first distillation column
14: upper out-put line
15, 25: dividing walls
16: lower out-put line
18: first benzene out-put line
20: second distillation column
24: cumene out-put line
26: polyisopropylbenzene (PIPB) stream out-put line
28: second benzene out-put line
30: third distillation column
34: PIPB out-put line
36: heavies out-put line
40: combining unit
42: benzene recycle line

MODES FOR INVENTION

Hereinafter, the apparatus and method for purifying cumene according to the present application will be described in more detail with reference to the accompanying drawings and an example.

In the present application, "and/or" is used to indicate that one or more of the components listed before or after are included.

In the present application, "connection", "installation", "combination", etc. refer to the two members which can be engaged with or disengaged from each other, as well as to an integral structure. Specifically, the terms such as "connection", "installation", "combination", etc. describe, for example, two members which are configured to be engaged with or disengaged from each other through a force-fit manner, a fitting manner using grooves and projections, a coupling manner using coupling members such as screws, bolts, pieces, rivets, brackets, etc., as well as an integral body of two members which become inseparable once combined through welding, an adhesive, an integral molding or the like.

The terms such as "first", "second", "third", "one end", "the other end", etc. in the present application are used to distinguish one element from the other, and it should be understood that each of the components is not limited by the above-described terms. Hereinafter, in the description of the present application, detailed descriptions of any related generic functions or configurations well-known in the art will be omitted.

In the present application, an "A stream" refers to a stream which includes at least an 'A' component, and it may include the 'A' component as a main component. For example, a "polyisopropylbenzene (PIPB) stream" is a stream which includes at least 'PIPB', and it may include 'PIPB' as a main component.

Meanwhile, the above-described 'including PIPB as a main component' may mean that PIPB is included the most among various components of the stream.

Also, in the present application, an "A/B stream" refers to a stream which includes at least an 'A' component and a 'B' component, and an "A/B/C stream" refers to a stream which includes at least an 'A' component, an 'B' component and a 'C' component. For example, "benzene/cumene/PIPB stream" may refer to a stream which includes at least 'benzene', 'cumene' and 'PIPB'.

The present application relates to an apparatus for purifying cumene. The apparatus for purifying cumene according to the present application may be installed in connection with, for example, a preparation apparatus of cumene.

In one example, the apparatus for purifying cumene according to the present application may be installed in connection with the alkylation reaction unit and trans alkylation reaction unit which constitute the preparation apparatus of cumene.

As described earlier, in the above-described alkylation reaction unit, benzene and propylene react to produce PIPBs such as DIPB, TIPB, etc.

In this case, the produced cumene is separated and recovered through a recovery line, and the stream including the above-described by-product is discharged through a separate line.

In addition to the above-described PIPB as a by-product, lights such as C3 (propylene, propane, etc.), etc., unrecovered cumene in a small amount, unconsumed benzene, water, other high-weight heavies, etc. are present in the stream discharged from the above-described alkylation reaction unit.

In addition, in the above-described trans alkylation reaction unit, polyalkylated benzene, which is the PIPB produced through the above-described side reaction, reacts with benzene to produce additional cumene. In the stream discharged from the above-described trans alkylation reaction unit, heavies which are heavier than PIPB are present in addition to PIPB.

The apparatus for purifying cumene according to the present application can take in a stream from the alkylation reaction unit and a stream from the trans alkylation reaction unit, and purify them as described above.

Specifically, the apparatus for purifying cumene according to the present application may take in a stream from the alkylation reaction unit and a stream from the trans alkylation reaction unit separately through distillation columns, which are different from each other.

In one example, the apparatus for purifying cumene according to the present application includes a first distillation column 10, a second distillation column 20 and a third distillation column 30. In this case, at least two of the three columns 10, 20 and 30 (for example, the first distillation column 10 and second distillation column 20) may be dividing wall columns (DWCs). In another example, the third distillation column 30 may also be a dividing wall column (DWC).

In a specific example, the first distillation column 10 takes in the stream from the alkylation reaction unit, and it may include a first benzene out-put line through which benzene is discharged and a lower out-put line through which the benzene/cumene/PIPB stream is discharged. The first benzene out-put line may be positioned, for example, in the central area of the first distillation column 10.

In a specific example, the second distillation column 20 takes in the stream from the trans alkylation reaction unit and the benzene/cumene/PIPB stream discharged from the lower out-put line of the first distillation column, and it may include a second benzene out-put line through which benzene is discharged and a PIPB stream out-put line through which a PIPB stream is discharged from the lower portion. The second benzene out-put line may be positioned, for example, above the second distillation column 20.

In a specific example, the third distillation column 30 takes in the PIPB stream discharged from the PIPB stream out-put line of the second dividing wall type distillation column, and it may include a PIPB out-put line through which PIPB is discharged from the upper portion and a heavies out-put line which discharges heavies from the lower portion.

Hereinafter, the apparatus for purifying cumene according to the present application will be described in more detail with reference to accompanying drawings.

FIG. 2 is an exemplifying diagram of the apparatus for purifying cumene according to the present application.

Referring to FIG. 2, the apparatus for purifying cumene according to the present application includes a first distillation column 10, a second distillation column 20 installed to the rear of the first distillation column 10, and a third distillation column 30 installed to the rear of the second distillation column 20.

In the present application, each of the columns 10, 20 and 30 may be selected from the distillation columns used in distillation processes in general industries, but at least the first distillation column 10 and second distillation column 20 may be of a dividing wall type. In addition, there is no particular limitation to the operating conditions of each of the columns 10, 20 and 30, for example, the plate number, inner diameter, pressure, temperature, reflux ratio of the upper and lower effluents, etc. of each of the columns 10, 20 and 30 in the present application, and they may be freely redesigned by an ordinary person skilled in the art within a range in which the objects of the present application can be achieved.

As shown in FIG. 2, a condenser and/or heat exchanger (or reboiler) may be installed in each of the columns 10, 20 and 30 of the present application. In FIG. 2, reference numeral C represents a condenser, whereas reference numeral B represents a heat exchanger (or reboiler).

In this case, the condenser C and/or heat exchanger B may be installed or not installed depending on each of the columns 10, 20 and 30.

In addition, the condenser C and heat exchanger B are, unless specified otherwise, the components which may be omitted even when illustrated in a diagram, or, conversely, they are the components which may be included (installed) even when not illustrated in a diagram.

The first distillation column 10 may include at least one or more in-put lines 11 and 12 installed in the front end portion.

In one example, the in-put lines 11 and 12 include an in-put line 12 for a stream from the alkylation reaction unit which takes in the stream discharged from the alkylation reaction unit.

In addition, in another exemplary embodiment, the in-put lines 11 and 12 may further include a benzene in-put line 11 which takes in fresh benzene. In other words, the apparatus for purifying cumene according to the present application may further include a benzene in-put line which is positioned at the front end portion and takes in fresh benzene.

When additional fresh benzene is introduced through the benzene in-put line 11, a cumene producing reaction may be promoted in the first distillation column 10 and/or second distillation column 20, increasing cumene yield.

FIG. 2 shows two in-put lines 11 and 12 installed at the front end portion of the first distillation column 10.

As illustrated in FIG. 2, the benzene in-put line 11 is installed roughly at the top of the first distillation column 10, the in-put line 12 for the stream from the alkylation reaction unit is installed below the benzene in-put line 11, and the in-put line 12 for the stream from the alkylation reaction unit may be installed roughly at the central area of the first distillation column 10, but they are not limited thereto.

In addition, the first distillation column 10 includes a first benzene out-put line 18 and a lower out-put line 16 installed at the lower portion. Benzene may be discharged through the first benzene out-put line 18, and the benzene/cumene/PIPB stream may be discharged through the lower out-put line 16.

Moreover, the first distillation column 10 may further include an upper out-put line 14, as illustrated in FIG. 2. In this case, a lights stream including light materials (lights) such as C3, etc. and water can be discharged and removed through the upper out-put line 14.

For example, in the first distillation column 10, it may be possible to separate the flow into three types including a lights stream containing lights and water; a benzene stream containing benzene; and a benzene/cumene/PIPB stream containing PIPB.

Among the above-described three types of flow, lights and water are discharged and removed through, for example, the upper out-put line 14, and benzene may be discharged through the benzene out-put line 18 to be recycled.

In one example, among the three types of flow, the benzene discharged through the first out-put line 18 may be supplied to the alkylation reaction unit and/or trans alkylation reaction unit to be recycled, or it may be recycled into the first distillation column 10 through the benzene in-put line 11.

Among the three types of flow, the benzene/cumene/PIPB stream may be discharged through, for example, the lower out-put line 16 and then introduced into the second distillation column 20.

The first distillation column 10 is a dividing wall type, as described earlier.

Inside the first distillation column 10, a dividing wall 15 is installed vertically.

In one example, the interior of the first distillation column 10 is partitioned by the dividing wall 15, and thus, it may include an in-put portion a into which the stream from the alkylation reaction unit is introduced, a column top section b from which lights and water are discharged, an out-put portion c from which benzene is discharged, and a column bottom section d from which the benzene/cumene/PIPB stream is discharged.

A dividing wall type distillation column (DWC) such as the above has a structure in which two distillation columns are integrated into one, and thus, the expenses invested in installation can be saved, and also, the amount of energy to be consumed per throughput can be aimed at a lower level as compared to the case where two distillation columns are used.

The second distillation column 20 is installed to the rear of the first distillation column 10, and it can separate the introduced stream into benzene and a PIPB stream. In addition, the second distillation column 20 may also separate cumene from the introduced stream to generate three types of flow including the above-described benzene and PIPB stream.

In one example, the second distillation column 20 may be a dividing wall type distillation column which takes in a stream from the trans alkylation reaction unit and a benzene/cumene/PIPB stream discharged from the lower out-put line of the first dividing wall type distillation column and includes a second benzene out-put line through which benzene is discharged from the upper portion and a PIPB stream out-put line through which a PIPB stream is discharged through the lower portion.

The second distillation column 20 may have an in-put line 22 for a stream from the trans alkylation reaction unit and a lower out-put line 16 of the first distillation column 10 connected to the front end portion.

The second distillation column 20 may include a second benzene out-put line 28 and a PIPB stream out-put line 26.

The second benzene out-put line 28 is positioned roughly on top of the second distillation column 20, and benzene may be discharged through it. In addition, the PIPB stream out-put line 26 is positioned below the second distillation column 20, and a PIPB stream may be discharged from it.

In addition, the second distillation column 20 may further include a cumene out-put line 24 installed roughly at the central area. Through such a cumene out-put line 24, cumene may be discharged.

Among the above-mentioned flows, the benzene discharged through the second benzene out-put line 28 may be recycled. For example, the benzene discharged through the second benzene out-put line 28 may be supplied to the alkylation reaction unit and/or trans alkylation reaction unit to be recycled, or it may be recycled through the benzene in-put line 11 into the first distillation column 10.

Among the above-mentioned flows, the cumene discharged through the cumene out-put line 24 may be recovered as a product. Specifically, the cumene discharged above may be sent to a storage tank after cooling and then recovered.

Among the above-mentioned flows, the PIPB stream discharged through the PIPB stream out-put line 26 may be introduced into the third distillation column 30.

The second distillation column 20 is a dividing wall type like the first distillation column 10.

Inside the second distillation column 20, a dividing wall 25 is installed vertically.

In one example, the inside of the second distillation column 20 is partitioned by the dividing wall 25, and thus, it may include an in-put portion a into which the stream from the alkylation reaction unit is introduced, a column top section b from which lights and water are discharged, an out-put portion c from which benzene is discharged, and a column bottom section d from which the benzene/cumene/PIPB stream is discharged.

In other words, the first distillation column and/or second distillation column are/is partitioned by the dividing wall(s)

installed inside, and thus, each may include an in-put portion into which the stream from the alkylation reaction unit is introduced, a column top section from which lights and water are discharged, an out-put portion from which benzene is discharged, and a column bottom section from which the benzene/cumene/PIPB stream is discharged.

The third distillation column 30 is installed to the rear of the second distillation column 20, and it may take in the PIPB stream discharged from the lower portion of the second distillation column 20 and separate them into PIPBs and heavies.

In one example, the third distillation column 30 may include a PIPB out-put line 34 installed at the upper portion and a heavies out-put line 36 installed at the lower portion.

The PIPBs separated in the third distillation column 30 are discharged from the upper portion through the out-put line 34, and the discharged PIPBs can be supplied, for example, to the trans alkylation reaction unit to be recycled.

The PIPB stream introduced from the second distillation column 2 may include PIPBs, for example, DIPB, TIPB, etc.

In this case, at least one among the above-described DIPB and TIPB (for example, DIPB) may be separated in the third distillation column 30, discharged through the out-put line 34, supplied to the trans alkylation reaction unit and recycled.

In addition, in another embodiment, the third distillation column 30 may include a plurality of PIPB out-put lines 34 which can separate PIPBs by type for separate discharges.

For example, the third distillation column 30 includes a TIPB out-put line installed at a plate having substantially a median plate number and a DIPB out-put line 34 installed at the upper portion, and thus, it can separate polyalkylation benzene by type at multiple plates.

Meanwhile, the heavies discharged through the heavies out-put line 36 are the heaviest materials in the process, and may specifically refer to materials heavier (materials having a higher boiling point) than PIPB. Such heavies may be discharged through the out-put line 36, cooled and then sent to a storage tank.

The apparatus for purifying cumene according to the present application includes three columns 10, 20 and 30 as described above, and, at least the first distillation column 10 and second distillation column 20 the among them are a dividing wall type.

In addition, the apparatus for purifying cumene according to the present application introduces the streams from the alkylation reaction unit and trans alkylation reaction unit into distillation columns which are different from each other. Also, the benzene to be discharged is not recovered by, separated in or discharged from a single column, but it is separated in and discharged from, for example, both of the first distillation column and second distillation column. Therefore, the amount of electricity consumed by a heat exchanger, a cooler, etc. which may be used additionally in a purification process can be saved.

More specifically, as benzene is separated in two dividing wall type distillation columns 10 and 20 through two steps, the load of benzene separation is reduced as compared to the case of a conventional separation in a single benzene column 1 (see FIG. 1), and thus, the amount of energy consumed can be reduced. In other words, when benzene was separated in one benzene column 1 in a conventional manner, supply of a large amount of heat energy was required to improve the separation efficiency of benzene. However, with the purification apparatus according to the present application, benzene is primarily separated in the first distillation column 10 and secondarily separated in the second distillation column 20 during the course of cumene separation, and thus, the heat energy (temperature of the heat source) supplied to the first distillation column 10 is consumed much less, thereby the amount of energy consumed can be reduced throughout the overall process. Moreover, a dividing wall type is adopted for both of the first distillation column 10 and second distillation column 20 in which benzene is separated, and therefore, the effect of energy savings can be further enhanced.

In addition, according to an exemplary embodiment, it is preferable that the first benzene out-put line 18 and second benzene out-put line 28 which are respectively installed in the first distillation column 10 and second distillation column 20 are operated in a way so that Mathematical Formula below is satisfied.

$$BZ_1/BZ_2 = 1.0 \text{ to } 3.0 \qquad \text{[Mathematical Formula]}$$

In the Mathematical Formula above, $BZ_1$ represents the flow amount of benzene discharged through the first benzene line 18, whereas $BZ_2$ represents the flow amount of benzene discharged through the second benzene out-put line 28.

In this case, there is no limitation to the actual value of the flow amount of benzene that passes through each of the out-put lines 18 and 28, and it is preferable that they have the flow amount ratio $BZ_1/BZ_2$ that satisfies the Mathematical Formula above.

When the flow amount ratio $BZ_1/BZ_2$ of benzene passing through each of the first benzene out-put line 18 and second benzene out-put line 28 satisfies the Mathematical Formula above, there may be a great advantage in the overall separation process as well as in terms of energy efficiency.

In other words, when the flow amount ratio $BZ_1/BZ_2$ is less than 1.0, it may be advantageous in terms of the reduction in the amount consumed among the energy supplied to the first distillation column 10, but in this case, the load is on the second distillation column 20, and the purity of cumene separated in the second distillation column 20 may degrade. In addition, when the flow amount ratio $BZ_1/BZ_2$ exceeds 3.0, the load is on the first distillation column 10, and thus, the effectiveness in reducing the amount of energy consumed may be negligible. Considering these points, the flow amount ratio $BZ_1/BZ_2$ of 1.0 to 3.0 is preferable.

The flow amount ratio $BZ_1/BZ_2$ may be adjusted, for example, by controlling the operating conditions of one or more selected among the first distillation column 10 and second distillation column 20 and amount of flow going in and/or out of each of the columns 10 and 20, etc., but it is not particularly limited thereto.

According to an exemplary embodiment, the flow amount ratio $BZ_1/BZ_2$ may be adjusted by controlling one or more operating conditions selected among the pressure(s), temperature(s), level(S), etc. of the first distillation column 10 and/or second distillation column 20.

In addition, the apparatus for purifying cumene according to the present application may further include a combining unit 40, through which the first benzene out-put line 18 and second benzene out-put line 28 are combined, and the benzene recycle line 42 which is connected to the combining unit 40. In this case, the benzene discharged through the first benzene out-put line 18 and second benzene out-put line 28 may be combined in the combining unit 40 and then supplied to one or more reaction units selected among the alkylation reaction unit and trans alkylation reaction unit.

In other words, the apparatus for purifying cumene according to the present application may further include a combining unit through which the first benzene out-put line and second benzene out-put line are combined; and a benzene recycle line supplying the benzene, which is combined in the combining unit, to one or more reaction units selected among the alkylation reaction unit and trans alkylation reaction unit.

According to the present application described above, as mentioned earlier, energy efficiency can increase by an improved purification process. Especially, with the benzene separated in two steps using two dividing wall type distillation columns 10 and 20, the amount of energy consumed can be reduced.

In addition, the connection of the in-put line 12 for the stream from the alkylation reaction unit to the first distillation column 10 and connection of the in-put line 22 for the stream from the trans alkylation reaction unit to the second distillation column 20 can also contribute to an improvement in the purification process.

Specifically, as in the prior art illustrated in FIG. 1, when both of two stream in-put lines 1b and 1c are connected to the benzene column 1, the load is on the benzene column, thus reducing efficiency in the separation process in the benzene column 1 itself and, furthermore, in carrying out the overall purification process continuously.

However, in the case of the apparatus for purifying cumene according to the present application, two streams are separately introduced into each of two columns 10 and 20, thus reducing the load on each of columns 10 and 20 and enabling a continuous and efficient purification process.

Meanwhile, in the present application, there is no limitation to the lines through which each of the above-described substances or streams is introduced or discharged, and they may be selected among metal tubes, plastic tubes, etc. Also, each line includes a flexible material. In addition, the lines may have a pump, etc. installed for a smooth flow of each substance and stream, or a valve, etc. installed to control the flow (shut down and/or control the flow amount).

The present application also relates to a method for purifying cumene using the above-described apparatus. The method for purifying cumene according to the present application includes a first separation process, a second separation process and a third separation process which are respectively carried out in the first distillation column, second distillation column and third distillation column.

In other words, the method for purifying cumene according to the present application includes a first separation process in which a stream from the alkylation reaction unit is introduced into the first distillation column, benzene is discharged through the first benzene out-put line, and the benzene/cumene/PIPB stream is discharged through the lower out-put line; a second separation process in which a stream from the trans alkylation reaction unit and the benzene/cumene/PIPB stream separated in the first separation process are introduced into the second dividing wall type distillation column, benzene is discharged through the second benzene out-put line, and the PIPB stream is discharged through the PIPB stream out-put line; and a third separation process in which the PIPB stream separated in the second separation process is introduced into the third distillation column, and PIPB s and heavies are separated.

The first separation process may be carried out in the first distillation column 10 and include the steps of introducing the stream from the alkylation reaction unit into the first distillation column, discharging benzene through, for example, the first benzene out-put line positioned roughly in the central area, and discharging the benzene/cumene/PIPB stream through the lower out-put line positioned at the lower portion. In addition, the first separation process may further include a step of discharging lights and water through the upper out-put line.

The stream introduced in the first separation stream may include a stream from the alkylation reaction unit and further include a stream which contains benzene to be introduced into the benzene in-put line which is mentioned earlier in regard to the first distillation column. In other words, the first separation process may further include a step of taking in benzene through the benzene in-put line installed at the front end portion.

The second separation process may be carried out in the second distillation column and include the steps of introducing a stream from the trans alkylation reaction unit into the second distillation column, discharging benzene through, for example, the second benzene out-put line positioned at the upper portion, and discharging PIPBs through the PIPB stream out-put line positioned at the lower portion. In addition, the second separation process may further include a step of discharging cumene through the cumene out-put line.

With the method for purifying cumene according to the present application, benzene separated through both of the first separation process and second separation process, thus saving the energy consumed.

In addition, with the method for purifying cumene according to the present application, two streams (for example, a stream from the alkylation reaction unit and a stream from the trans alkylation reaction unit) are separately introduced into each of the two columns 10 and 20, thus the load on each of columns 10 and 20 is reduced, enabling a continuous and efficient purification process.

Also, the method for purifying cumene according to the present application may further include the steps of combining the benzene discharged from the first benzene out-put line and second benzene out-put line and then supplying the combined benzene to any one or more reaction units selected among the alkylation reaction unit and trans alkylation reaction unit.

Here, the first separation process and second separation process may satisfy Mathematical Formula 1 below.

$$BZ_1/BZ_2 = 1.0 \text{ to } 3.0 \qquad \text{[Mathematical Formula 1]}$$

In the Mathematical Formula 1 above, $BZ_1$ represents the flow amount of benzene discharged through the first benzene line, whereas $BZ_2$ represents the flow amount of benzene discharged through the second benzene out-put line.

When the flow amount ratio $BZ_1/BZ_2$ of benzene passing through each of the first benzene out-put line 18 and second benzene out-put line 28 satisfies the above Mathematical Formula 1, there may be a great advantage in the overall separation process as well as in terms of energy efficiency.

Hereinafter, an example of the present application and a comparative example will be provided. The example below is provided merely to help understanding of the present application, and it should not be understood as limiting the technical scope of the present application.

Example 1

Cumene was purified using an apparatus as shown in FIG. 4.

The apparatus shown in FIG. 4 is identical to the apparatus shown in FIG. 2, but in FIG. 4, Q was specified for the description of the heat energy consumed in each of columns 10 and 20.

Referring to FIG. 4, fresh benzene 11 and a stream 12 which was discharged from the alkylation reaction unit were introduced through each of two in-put lines 11 and 12 into the first distillation column 10.

In the first distillation column 10, lights and water were removed through the upper out-put line 14, and benzene was discharged through the first benzene out-put line 18 in the center. Also, the stream from the lower portion was introduced to the second distillation column 20 through the lower out-put line 16.

To the second distillation column 20, a stream 22 discharged from the trans alkylation reaction unit was introduced along with the lower stream 16 from the first distillation column 10. Also, benzene was discharged through the second benzene out-put line 28 from the upper portion, and cumene was discharged through the cumene out-put line 24 from the central area. At the same time, the polyisopropylbenzene stream discharged through the lower out-put line 26 was introduced to the third distillation column 30.

In addition, polyisopropylbenzene is discharged through the upper out-put line 34 of the third distillation column 30 to be recycled into the trans alkylation unit, and heavies were discharged through the lower out-put line 36 and then cooled. In this case, a dividing wall type distillation column (DWC) was adopted for the first distillation column 10 and second distillation column 20, and the flow amount ratio $BZ_1/BZ_2$ of the flow amount of benzene $BZ_1$ passing through the first benzene out-put line 18 and flow amount of benzene $BZ_2$ passing through the second benzene out-put line 28 was set at 2.

The purification process as the above was performed under a stabilized condition, and the heat energy $Q_1$ supplied to the first distillation column 10 and heat energy $Q_2$ supplied to the second distillation column 20 were measured. The results are shown in Table 1 below.

Example 2

The purification process for cumene was performed in the same manner as in Example 1, except that the flow amount ratio $BZ_1/BZ_2$ of the flow amount of benzene $BZ_1$ passing through the first benzene out-put line 18 and flow amount of benzene $BZ_2$ passing through the second benzene out-put line 28 was set at 1 by making changes to the internal pressures, temperatures and levels of the first distillation column 10 and second distillation column 20. The heat energy $Q_1$ supplied to the first distillation column 10 and heat energy $Q_2$ supplied to the second distillation column 20 were measured. The results are shown in Table 1 below.

Example 3

The purification process for cumene was performed in the same manner as in Example 1, except that the flow amount ratio $BZ_1/BZ_2$ of the flow amount of benzene $BZ_1$ passing through the first benzene out-put line 18 and flow amount of benzene $BZ_2$ passing through the second benzene out-put line 28 was set at 3 by making changes to the internal pressures, temperatures and levels of the first distillation column 10 and second distillation column 20. The heat energy $Q_1$ supplied to the first distillation column 10 and heat energy $Q_2$ supplied to the second distillation column 20 were measured. The results are shown in Table 1 below.

Example 4

The purification process for cumene was performed in the same manner as in Example 1, except that the flow amount ratio $BZ_1/BZ_2$ of the flow amount of benzene $BZ_1$ passing through the first benzene out-put line 18 and flow amount of benzene $BZ_2$ passing through the second benzene out-put line 28 was set at 0.5 by making changes to the internal pressures, temperatures and levels of the first distillation column 10 and second distillation column 20. The heat energy $Q_1$ supplied to the first distillation column 10 and heat energy $Q_2$ supplied to the second distillation column 20 were measured. The results are shown in Table 1 below.

Example 5

The purification process for cumene was performed in the same manner as in Example 1, except that the flow amount ratio $BZ_1/BZ_2$ of the flow amount of benzene $BZ_1$ passing through the first benzene out-put line 18 and flow amount of benzene $BZ_2$ passing through the second benzene out-put line 28 was set at 3.5 by making changes to the internal pressures, temperatures and levels of the first distillation column 10 and second distillation column 20. The heat energy $Q_1$ supplied to the first distillation column 10 and heat energy $Q_2$ supplied to the second distillation column 20 were measured. The results are shown in Table 1 below.

Comparative Example

Cumene was purified using an apparatus as shown in FIG. 3.

The apparatus shown in FIG. 3 is identical to the apparatus shown in FIG. 1, but in FIG. 3, Q was specified for the description of the heat energy consumed in each of columns 1 and 2.

Comparative Example is a conventional and general process, and description of the specific process well-known in the art will be omitted.

Referring to FIG. 3, fresh benzene 1a, a stream 1b discharged from an alkylation reaction unit and a stream 1c discharged from a trans alkylation reaction unit were introduced to a first distillation column 1 respectively through each of in-put lines 1a, 1b and 1c. Also, discharges of lights and water through an upper out-put line 1d, benzene through a central out-put line 1f and a cumene stream through a lower out-put line 1e were carried out.

In addition, cumene was discharged through an out-put line 2a at the upper portion of a second distillation column 2 to be recovered, and a polyisopropylbenzene stream discharged through an out-put line 2b at the lower portion was introduced to a third distillation column 3. Also, polyisopropylbenzene was discharged through an out-put line 3a at the upper portion of the third distillation column 3 to be recycled into a trans alkylation reaction unit, and heavies were discharged through an out-put line 3d at the lower portion and cooled.

The purification process as the above was performed under a stabilized condition, and the heat energy $Q_1$ supplied to a first distillation column 1 and heat energy $Q_2$ supplied to a second distillation column 2 were measured. The results are shown in [Table 1] below.

TABLE 1

| Note | Flow amount ratio ($BZ_1/BZ_2$) | $Q_1$ | $Q_2$ | $Q_T$ | Amount saved ($\Delta Q$) |
|---|---|---|---|---|---|
| Comparative Example | — | 8.4 | 5.2 | 13.6 | — |

TABLE 1-continued

| Note | Flow amount ratio ($BZ_1/BZ_2$) | $Q_1$ | $Q_2$ | $Q_T$ | Amount saved ($\Delta Q$) |
|---|---|---|---|---|---|
| Example 1 | 2 | 3.5 | 8.4 | 11.9 | 1.7 |
| Example 2 | 1 | 2.6 | 9.7 | 12.3 | 1.3 |
| Example 3 | 3 | 4.7 | 7.8 | 12.5 | 1.1 |
| Example 4 | 0.5 | 2.5 | 10.5 | 13.0 | 0.6 |
| Example 5 | 3.5 | 5.5 | 7.7 | 13.2 | 0.4 |

$Q_1$ : heat energy supplied to first distillation column (Gcal/hr)
$Q_2$ : heat energy supplied to second distillation column (Gcal/hr)
$Q_T$ : sum of $Q_1$ and $Q_2$ (Gcal/hr)

As shown in [Table 1] above, it can be seen that heat energy was efficiently reduced when two DWCs were used, the streams from the alkylation reaction unit and trans alkylation reaction unit were separately introduced into each of the two columns, and benzene was separated through two steps, according to Examples 1 to 5. For example, in the case of Example 1, it was found that the amount saved as compared to the conventional process (Comparative Example) was 1.7 Gcal/hr (saved by about 12.5%).

In addition, as shown in [Table 1] above, it can be seen that the amount of energy saved varied depending on the flow amount ratio $BZ_1/BZ_2$ of benzene. Especially, when the flow amount ratio $BZ_1/BZ_2$ of benzene is in the range of 1.0 to 3.0 (Examples 1 to 3), more energy was saved compared to the opposite cases (Examples 4 and 5).

The invention claimed is:

1. An apparatus for purifying cumene comprising:
a first dividing wall type distillation column which takes in a stream from an alkylation reactor and comprises a first benzene output line through which benzene is discharged and a benzene/cumene/polyisopropylbenzene stream output line through which a benzene/cumene/polyisopropylbenzene stream is discharged;
a second dividing wall type distillation column which takes in a stream from a transalkylation reactor and the benzene/cumene/polyisopropylbenzene stream discharged through the benzene/cumene/polyisopropylbenzene stream output line of the first dividing wall type distillation column, includes a transalkylation reactor stream input line through which the stream from the transalkylation reactor is introduced, a benzene/cumene/polyisopropylbenzene stream input line through which the benzene/cumene/polyisopropylbenzene stream is introduced, a second benzene output line through which benzene is discharged, and includes a first polyisopropylbenzene stream output line through which a polyisopropylbenzene stream is discharged; and
a third distillation column which takes in the polyisopropylbenzene stream discharged through the first polyisopropylbenzene stream output line of the second dividing wall type distillation column, includes a second polyisopropylbenzene output line through which polyisopropylbenzene is discharged, and includes a heavies output line through which heavy materials are discharged,
wherein the first benzene output line and the second benzene output line are operated in a way so that Mathematical Formula 1 below is satisfied,
wherein a flow amount ratio $BZ_1/BZ_2$ of the Mathematical Formula 1 is adjusted by controlling at least one selected from operating conditions of the first and second dividing wall type distillation columns, and amounts of flow going in and out of the first and second dividing wall type distillation columns,
wherein operating conditions of the first and second dividing wall type distillation columns are selected from a pressure, a temperature, and a level:

$$BZ_1/BZ_2 = 1.0 \text{ to } 3.0 \qquad \text{[Mathematical Formula 1]}$$

where in the Mathematical Formula 1 above, $BZ_1$ represents a flow amount of benzene discharged through the first benzene output line and $BZ_2$ represents a flow amount of benzene discharged through the second benzene output line.

2. The apparatus of claim 1, wherein the first dividing wall type distillation column further includes a light materials and water output line through which light materials and water are discharged.

3. The apparatus of claim 1, wherein the first dividing wall type distillation column includes a benzene input line which takes in fresh benzene.

4. The apparatus of claim 1, wherein the second dividing wall type distillation column further includes a cumene output line through which cumene is discharged.

5. The apparatus of claim 1, further comprising:
a combiner through which the first benzene output line and the second benzene output line are combined; and
a benzene recycle line through which benzene combined in the combiner is supplied to one or more reactors selected among the alkylation reaction unit reactor and the transalkylation reactor.

6. The apparatus of claim 1, wherein the first dividing wall type distillation column and the second dividing wall type distillation column are/is partitioned by a dividing wall, the first dividing wall type distillation column includes an input portion into which the stream from the alkylation reactor is introduced, a column top section from which light materials and water are discharged, an output portion from which benzene is discharged, and a column bottom section from which the benzene/cumene/polyisopropylbenzene stream is discharged.

7. A method for purifying cumene, the method comprising:
a first separation step wherein a stream from an alkylation reactor is introduced into a first dividing wall type distillation column, benzene is discharged through a first benzene output line, and a benzene/cumene/polyisopropylbenzene stream is discharged through a benzene/cumene/polyisopropylbenzene stream output line;
a second separation step wherein a stream from a transalkylation reactor and the benzene/cumene/polyisopropylbenzene stream separated during the first separation step are introduced into a transalkylation reactor stream input line and a benzene/cumene/polyisopropylbenzene stream input line of a second dividing wall type distillation column, benzene is discharged through a second benzene output line, and a polyisopropylbenzene stream is discharged through a first polyisopropylbenzene stream output line; and
a third separation step wherein the polyisopropylbenzene stream separated during the second separation step is introduced into a third distillation column, and polyisopropylbenzene and heavy materials are separated, polyisopropylbenzene is discharged through a second polyisopropylbenzene output line and heavy materials are discharged through a heavies output line,
wherein the first separation step and second separation step satisfy Mathematical Formula 1 below, wherein a flow amount ratio $BZ_1/BZ_2$ of the Mathematical Formula 1 is adjusted by controlling at least one selected from operating conditions of the first and second dividing wall type distillation columns, and amounts of flow going in and out of the first and second dividing wall type distillation columns, wherein operating conditions of the first and second dividing wall type distillation columns are selected from a pressure, a temperature, and a level:

$$BZ_1/BZ_2 = 1.0 \text{ to } 3.0 \quad \text{[Mathematical Formula 1]}$$

where in the Mathematical Formula 1 above, $BZ_1$ represents a flow amount of benzene discharged through the first benzene output line and $BZ_2$ represents a flow amount of benzene discharged through the second benzene output line.

8. The method of claim 7, wherein the first separation step further includes discharging light materials and water through a light materials and water output line of the first dividing wall type distillation column.

9. The method of claim 7, wherein the first separation step further includes taking in benzene through a benzene input line installed at the first dividing wall type distillation column.

10. The method of claim 7, wherein the second separation step further includes discharging cumene through a cumene output line of the second dividing wall type distillation column.

11. The method of claim 7, further comprising a step of:
   combining benzene discharged from the first benzene output line and second benzene output line; and
   supplying the combined benzene to one or more reactors selected among the alkylation reactor and transalkylation reactor.

* * * * *